United States Patent
Chou

(10) Patent No.: US 7,344,864 B2
(45) Date of Patent: Mar. 18, 2008

(54) DROSOPHILA CLIPPED FRT (CFRT) CHROMOSOME INSENSITIVE TO P TRANSPOSAGE, GENERATING METHOD THEREOF, AND APPLICATION THEREOF

(76) Inventor: Tze-Bin Chou, 11th Fl., No. 405, 38th Neighborhood, Leshan Tsuen, Gueishan Shiang, Taoyuan (TW)

( * ) Notice: Subject to any disclaimer, the term of this patent is extended or adjusted under 35 U.S.C. 154(b) by 486 days.

(21) Appl. No.: 10/690,176

(22) Filed: Oct. 20, 2003

(65) Prior Publication Data

US 2004/0064262 A1   Apr. 1, 2004

Related U.S. Application Data

(62) Division of application No. 10/044,423, filed on Jan. 10, 2002, now Pat. No. 6,962,804.

(51) Int. Cl.
*C12P 19/34* (2006.01)
*C12N 15/63* (2006.01)
(52) U.S. Cl. ............... 435/91.1; 435/6; 435/89; 536/23.1; 536/24.1
(58) Field of Classification Search ............... None
See application file for complete search history.

(56) References Cited

OTHER PUBLICATIONS

Chou and Perrimon. Use of a Yeast Site-Specific Recombinase to Produce Female Germline Chimeras in *Drosophila* Genetics 131:643-653 (1992).
Chou et al. "Autosomal P[ovo$^{D1}$] Dominant Female-Sterile Insertions in *Drosophila* anf Their Use in Generating Germ-Line Chimeras" Development 119:1359-1369 (1993).
Chou and Perrimon. "The Autosomal FLP-DFS Technique for Generating Germline Mosaics in *Drosophila melanogaster*" Genetics 144:1673-1679 (1996).
Duffy et al. "Identifying Loci Required for Follicular Patterning Using Directed Mosaics" Development 125:2263-71 (1998).
Golic and Lindquist. "The FLP Recombinase of Yeast Catalyzes Site-Specific Recombination in the *Drosophila* Genome" Cell 59:499-509 (1989).
Hutchison et al. "Global Transposon Mutagenesis and a Minimal Mycoplasma Genome" Science 286:2165-69 (1999).
Li et al. "Leukaemia Disease Genes: Large-Scale Cloning and Pathway Predictions" Nature Genetics 23:348-353 (1999).
Perrimon et al. "Zygotic Lethals with Specific Maternal Effect Phenotypes in *Drosophila melanogaster*. I. Loci on the X Chromosome" Genetics 121:333-352 (1996).
Robertson et al. "A Stable Genomic Source of P Element Transposase in *Drosophila melanogaster*" Genetics 118(3):461-70 (1988).
Spradling. "The Berkeley *Drosophila* Genome Project Gene Disruption Project: Single P-Element Insertions Mutating 25% of Vital *Drosophila* Genes" Genetics 153:135-177 (1999).
Xu and Rubin. "Analysis of Genetic Mosaics in Developing and Adult *Drosophila* Tissues" Development 117:1223-1237 (1993).
Zhang and Spradling. "Efficient and Dispersed Local P Element Transposition from *Drosophila* Females" Genetics 133:361-373 (1993).

*Primary Examiner*—Nancy Vogel
*Assistant Examiner*—Michele K. Joike
(74) *Attorney, Agent, or Firm*—Morrison & Foerster LLP

(57) ABSTRACT

A method for generating a *Drosophila* clipped FRT (cFRT) chromosome is provided, wherein the chromosome is insensitive to a P transposase but remains functional to a yeast site-specific flippase recombinase (FLP). The method includes steps of: (a) exposing a FRT chromosome to the P transposase for occurring a local and imprecise transposition, wherein the FRT chromosome contains a P[FRT] insertion with a selection marker gene, (b) screening the P[FRT] insertion insensitive to the P transposase to obtain screened products, (c) selecting candidate products from the screened products by further examinations, and (d) exposing the candidate products by the P transposase and selecting a desired product by the further examinations to obtain the *Drosophila* clipped FRT (cFRT) chromosome insensitive to the P transposase but remaining functional to the yeast site-specific flippase recombinase. The cFRT$^{2L2R}$ chromosome can be used as the direct target in the direct P-transposon-induced mutagenesis.

4 Claims, 6 Drawing Sheets

SEQUENCE LISTING

<160> NUMBER OF SEQ ID NOS: 35

<210> SEQ ID NO 1
<211> LENGTH: 20
<212> TYPE: DNA
<213> ORGANISM: Artificial Sequence
<220> FEATURE:
<223> OTHER INFORMATION: Synthetic Construct

<400> SEQUENCE: 1
catgatgaaa taacataagg                20

<210> SEQ ID NO 2
<211> LENGTH: 20
<212> TYPE: DNA
<213> ORGANISM: Artificial Sequence

```
<220> FEATURE:
<223> OTHER INFORMATION: Synthetic Construct

<400> SEQUENCE: 2
ccgtcgaaag ccgaagctta                                              20

<210> SEQ ID NO 3
<211> LENGTH: 23
<212> TYPE: DNA
<213> ORGANISM: Artificial Sequence
<220> FEATURE:
<223> OTHER INFORMATION: Synthetic Construct

<400> SEQUENCE: 3
cccaaggctc tgctcccaca att                                          23

<210> SEQ ID NO 4
<211> LENGTH: 20
<212> TYPE: DNA
<213> ORGANISM: Artificial Sequence
<220> FEATURE:
<223> OTHER INFORMATION: Synthetic Construct

<400> SEQUENCE: 4
aaaccccacg gacatgctaa                                              20

<210> SEQ ID NO 5
<211> LENGTH: 20
<212> TYPE: DNA
<213> ORGANISM: Artificial Sequence
<220> FEATURE:
<223> OTHER INFORMATION: Synthetic Construct

<400> SEQUENCE: 5
cggcaagaga catccactta                                              20

<210> SEQ ID NO 6
<211> LENGTH: 24
<212> TYPE: DNA
<213> ORGANISM: Artificial Sequence
<220> FEATURE:
<223> OTHER INFORMATION: Synthetic Construct

<400> SEQUENCE: 6
cacccaaggc tctgctccca caat                                         24

<210> SEQ ID NO 7
<211> LENGTH: 26
<212> TYPE: DNA
<213> ORGANISM: Artificial Sequence
<220> FEATURE:
<223> OTHER INFORMATION: Synthetic Construct

<400> SEQUENCE: 7
ccttagcatg tccgtggggt ttgaat                                       26

<210> SEQ ID NO 8
<211> LENGTH: 28
<212> TYPE: DNA
<213> ORGANISM: Artificial Sequence
<220> FEATURE:
<223> OTHER INFORMATION: Synthetic Construct

<400> SEQUENCE: 8
cttgccgacg ggaccacctt atgttatt                                     28
```

<210> SEQ ID NO 9
<211> LENGTH: 25
<212> TYPE: DNA
<213> ORGANISM: Artificial Sequence
<220> FEATURE:
<223> OTHER INFORMATION: Synthetic Construct

<400> SEQUENCE: 9
gaattcactg gccgtcgttt tacaa                                         25

<210> SEQ ID NO 10
<211> LENGTH: 22
<212> TYPE: DNA
<213> ORGANISM: Artificial Sequence
<220> FEATURE:
<223> OTHER INFORMATION: Synthetic Construct

<400> SEQUENCE: 10
acacaacctt tcctctcaac aa                                            22

<210> SEQ ID NO 11
<211> LENGTH: 24
<212> TYPE: DNA
<213> ORGANISM: Artificial Sequence
<220> FEATURE:
<223> OTHER INFORMATION: Synthetic Construct

<400> SEQUENCE: 11
gagtacgcaa agctttaact atgt                                          24

<210> SEQ ID NO 12
<211> LENGTH: 21
<212> TYPE: DNA
<213> ORGANISM: Artificial Sequence
<220> FEATURE:
<223> OTHER INFORMATION: Synthetic Construct

<400> SEQUENCE: 12
cgacgagttg cttctcccac a                                             21

<210> SEQ ID NO 13
<211> LENGTH: 21
<212> TYPE: DNA
<213> ORGANISM: Artificial Sequence
<220> FEATURE:
<223> OTHER INFORMATION: Synthetic Construct

<400> SEQUENCE: 13
gtttccctcg cactgctatt t                                             21

<210> SEQ ID NO 14
<211> LENGTH: 20
<212> TYPE: DNA
<213> ORGANISM: Artificial Sequence
<220> FEATURE:
<223> OTHER INFORMATION: Synthetic Construct

<400> SEQUENCE: 14
ccgtcgaaag ccgaagctta                                               20

<210> SEQ ID NO 15
<211> LENGTH: 23
<212> TYPE: DNA
<213> ORGANISM: Artificial Sequence
<220> FEATURE:
<223> OTHER INFORMATION: Synthetic Construct

```
<400> SEQUENCE: 15
cccaaggctc tgctcccaca att                                              23

<210> SEQ ID NO 16
<211> LENGTH: 18
<212> TYPE: DNA
<213> ORGANISM: Artificial Sequence
<220> FEATURE:
<223> OTHER INFORMATION: Synthetic Construct

<400> SEQUENCE: 16
cgcacggttt caatcaca                                                    18

<210> SEQ ID NO 17
<211> LENGTH: 21
<212> TYPE: DNA
<213> ORGANISM: Artificial Sequence
<220> FEATURE:
<223> OTHER INFORMATION: Synthetic Construct

<400> SEQUENCE: 17
ggttacgagg cagcagttct a                                                21

<210> SEQ ID NO 18
<211> LENGTH: 20
<212> TYPE: DNA
<213> ORGANISM: Artificial Sequence
<220> FEATURE:
<223> OTHER INFORMATION: Synthetic Construct

<400> SEQUENCE: 18
aacgcccact tccgtattgc                                                  20

<210> SEQ ID NO 19
<211> LENGTH: 21
<212> TYPE: DNA
<213> ORGANISM: Artificial Sequence
<220> FEATURE:
<223> OTHER INFORMATION: Synthetic Construct

<400> SEQUENCE: 19
aatcctggtg cttgctttcc t                                                21

<210> SEQ ID NO 20
<211> LENGTH: 19
<212> TYPE: DNA
<213> ORGANISM: Artificial Sequence
<220> FEATURE:
<223> OTHER INFORMATION: Synthetic Construct

<400> SEQUENCE: 20
gtaggtcatt tgtttggca                                                   19

<210> SEQ ID NO 21
<211> LENGTH: 17
<212> TYPE: DNA
<213> ORGANISM: Artificial Sequence
<220> FEATURE:
<223> OTHER INFORMATION: Synthetic Construct

<400> SEQUENCE: 21
ctgatgccgc cgtgttc                                                     17

<210> SEQ ID NO 22
```

```
<211> LENGTH: 21
<212> TYPE: DNA
<213> ORGANISM: Artificial Sequence
<220> FEATURE:
<223> OTHER INFORMATION: Synthetic Construct

<400> SEQUENCE: 22
ccccgcatgg aatgggataa t                                              21

<210> SEQ ID NO 23
<211> LENGTH: 16
<212> TYPE: DNA
<213> ORGANISM: Artificial Sequence
<220> FEATURE:
<223> OTHER INFORMATION: Synthetic Construct

<400> SEQUENCE: 23
agtccggtgc gttttt                                                    16

<210> SEQ ID NO 24
<211> LENGTH: 20
<212> TYPE: DNA
<213> ORGANISM: Artificial Sequence
<220> FEATURE:
<223> OTHER INFORMATION: Synthetic Construct

<400> SEQUENCE: 24
aaaccccacg gacatgctaa                                                20

<210> SEQ ID NO 25
<211> LENGTH: 20
<212> TYPE: DNA
<213> ORGANISM: Artificial Sequence
<220> FEATURE:
<223> OTHER INFORMATION: Synthetic Construct

<400> SEQUENCE: 25
cggcaagaga catccactta                                                20

<210> SEQ ID NO 26
<211> LENGTH: 17
<212> TYPE: DNA
<213> ORGANISM: Artificial Sequence
<220> FEATURE:
<223> OTHER INFORMATION: Synthetic Construct

<400> SEQUENCE: 26
tgctcgcttg gatgaac                                                   17

<210> SEQ ID NO 27
<211> LENGTH: 17
<212> TYPE: DNA
<213> ORGANISM: Artificial Sequence
<220> FEATURE:
<223> OTHER INFORMATION: Synthetic Construct

<400> SEQUENCE: 27
agtggagtgg gagtgga                                                   17

<210> SEQ ID NO 28
<211> LENGTH: 20
<212> TYPE: DNA
<213> ORGANISM: Artificial Sequence
<220> FEATURE:
<223> OTHER INFORMATION: Synthetic Construct

<400> SEQUENCE: 28
```
ccgtcgaaag ccgaagctta                          20

<210> SEQ ID NO 29
<211> LENGTH: 23
<212> TYPE: DNA
<213> ORGANISM: Artificial Sequence
<220> FEATURE:
<223> OTHER INFORMATION: Synthetic Construct

<400> SEQUENCE: 29
cccaaggctc tgctcccaca att                      23

<210> SEQ ID NO 30
<211> LENGTH: 21
<212> TYPE: DNA
<213> ORGANISM: Artificial Sequence
<220> FEATURE:
<223> OTHER INFORMATION: Synthetic Construct

<400> SEQUENCE: 30
ccccgcatgg aatgggataa t                        21

<210> SEQ ID NO 31
<211> LENGTH: 16
<212> TYPE: DNA
<213> ORGANISM: Artificial Sequence
<220> FEATURE:
<223> OTHER INFORMATION: Synthetic Construct

<400> SEQUENCE: 31
agtccggtgc gttttt                              16

<210> SEQ ID NO 32
<211> LENGTH: 20
<212> TYPE: DNA
<213> ORGANISM: Artificial Sequence
<220> FEATURE:
<223> OTHER INFORMATION: Synthetic Construct

<400> SEQUENCE: 32
aaaccccacg gacatgctaa                          20

<210> SEQ ID NO 33
<211> LENGTH: 20
<212> TYPE: DNA
<213> ORGANISM: Artificial Sequence
<220> FEATURE:
<223> OTHER INFORMATION: Synthetic Construct

<400> SEQUENCE: 33
cggcaagaga catccactta                          20

<210> SEQ ID NO 34
<211> LENGTH: 36
<212> TYPE: DNA
<213> ORGANISM: Artificial Sequence
<220> FEATURE:
<223> OTHER INFORMATION: Synthetic Construct

<400> SEQUENCE: 34
tatatacatt tatcgagcta tcgagctata attcct        36

<210> SEQ ID NO 35
<211> LENGTH: 35
<212> TYPE: DNA

```
-continued

<213> ORGANISM: Artificial Sequence
<220> FEATURE:
<223> OTHER INFORMATION: Synthetic Construct

<400> SEQUENCE: 35
cttgatttgt gcccggttgc ccggttctat tggct                                    35
```

DROSOPHILA CLIPPED FRT (CFRT) CHROMOSOME INSENSITIVE TO P TRANSPOSAGE, GENERATING METHOD THEREOF, AND APPLICATION THEREOF

CROSS-REFERENCE TO RELATED APPLICATION

This application is a divisional application of application Ser. No. 10/044,423, filed Jan. 10, 2002 now U.S. Pat. No. 6,962,804, the entire contents of which is hereby incorporated herein by reference.

FIELD OF THE INVENTION

The present invention is related to a Drosophila clipped FRT (cFRT) chromosome, and more particularly, to a Drosophila clipped FRT (cFRT) chromosome insensitive to P transposase but remaining functional to yeast site-specific flippase recombinase (FLP), the generating method thereof, and the application thereof.

BACKGROUND OF THE INVENTION

The human diseases, the screening of the pathogenic genes and the functional research thereof are always important research fields. However, due to the systematic limitation, the possible living mechanisms are understood mostly through animal models which contain manipulated genes. For hundreds of years, Drosophila Melanogaster have been used as the basic source material for teaching and genetics study. In the last few decades, since the molecular biology method was brought into this field, the research of Drosophila molecular developmental genetics has entered into a new stage. The biological mechanism of Drosophila is very evolutionarily conserved. Therefore, from Drosophila study, people have come to understand that many human disease genes and cancer-related genes are derived from the gene mutation which controls the developmental mechanism. For example, the initiative mechanism of colon cancer and its complex working process are understood by studying the related genes of Wingless pathway which drives the development of abdominal segment formation in Drosophila embryo. Therefore, the main future studying direction of the present invention is doing the searching and studying of the specific functional genes in Drosophila genome based on the technique of the present invention. The Drosophila model will then be the base of searching the homologous genes of the human disease and pathogenic genes for the further study of human genetic mechanism.

In the present time, as the structural genomic projects in model organisms are completed, how to decipher a large amount of raw DNA sequences data in understanding gene function in vivo will be one of the major tasks for biology-related researchers. Different genomic strategies for defining and dissecting developmental and physiological pathways have been approached. The summit of these approaches is the systematic genomic screening of a specific functional trait using DNA tags such as P-transposon or retrovirus as mutagenesis agents. The designed transposon can be used as a mobile element to rapidly obtain cellular DNA sequence nearby the genetic mutation. The cellular DNA sequences can be obtained from the P-transposon-induced mutated genes loci by the direct use of inverse PCR (IPCR) or plasmid rescue methods. By such operating way, the inefficient and labor-intensive drill of cloning sequences for obtaining the junction sequence between the host and the mobile element can be circumvented. While retrovirus was used to mutate leukemia-causing genes in mouse (Li et al., 1999, Nature Genetics 23, 348), several hundred integration sites were cloned and characterized followed by high-throughput sequencing, data analysis and refined genetic mapping. Similarly, a global transposon mutagenesis in Mycoplasma allowed the question of the number of essential genes in a minimal genome to be answered (Hutchison, et al., 1999, Science 286, 2165). Therefore, by combining with emerging genomic tools, such systems in model organisms will indeed dramatically accelerate the pace of discovery in human disease-genes and cancer-related genes.

For the functional study of Drosophila genes, a conventional approach relies on the creation of mosaic animals whereby the genotype varies in a cell-specific or tissue-specific manner. Currently, various techniques utilize the yeast FLP-FRT recombination system introduced into Drosophila (Golic and Lindquist, 1989, Cell 59, 499) to promote chromosomal site-specific exchange. This system allows the efficient recovery of homozygous patches in an otherwise heterozygous animal and thus permits a phenotypic analysis of mutant tissues.

Different versions of the FLP-FRT (Fippase-Flippase Recombination Target sequence) system have been established for analyzing gene functions in either somatic or germline tissues. The direct mosaic productions in different somatic tissues have been established (Xu and Rubin, 1993, Development 117, 1223; Duffy et al., 1998, Development 125, 2263). In these methods, different tracing markers are used as the controls to monitor the presence of homozygous clones of genes to be studied. In addition, the FLP-DFS technique suitable for asking germline functions for loci residing in more than 95% of the genome has also been systematically completed (Chou and Perrimon, 1992, Genetics 131, 643; Chou et al., 1993, Development, 119, 1359 and Chou and Perrimon, 1996, Genetics 144, 1673). The FLP-DFS technique uses the X-linked germline-dependent dominant female sterile mutation ovo$^{D1}$ as a selection marker for the detection of germline recombination events. Nevertheless, the FLP-FRT system is used to promote site-specific chromosomal exchange (Chou and Perrimon, 1992, Genetics 131, 643).

However, the major drawback for all of these FLP-FRT methods is that the mobile element such as the P-transposon can not be used directly as the mutagenesis agent to mutate the FRT chromosomes. While Δ2-3 transposase is recognizing the P transposon insertion as the mobilization origin, it simultaneously recognizes and transposes the P[FRT] insertions used in the FLP-FRT system. Under such situation, the genetic recombination cannot proceed due to the fact that the P[FRT] chromosomes are not homologous. For example, the mobilized P[FRT] will mostly create a non-homologous condition. However, the germline recombination of P[FRT]-ovo$^{D1}$ chromosome needs the existence of the homologous P[FRT] chromosome when P[FRT]-ovo$^{D1}$ chromosome is used for the FLP-DFS germline recombination. Therefore, the transposition of the P[FRT] insertion results in a non-homologous condition so that the germline recombination cannot proceed.

Presently, only EMS-based methods can be used for a full-scale genome-wide screening when using FRT chromosomes. Many interesting genes have been recovered. However, the goal to completely recover and to do molecular characterization of all interesting loci efficiently would be difficult if only EMS-based methods are used for mutagenesis. Because EMS produces mostly point mutations, it does not create any molecular tags on mutated genes for cloning manipulation. Consequently, the approach for identifying important genes is heavily impeded by the inefficient and labor-intensive traditional molecular cloning procedures.

Another alternative strategy to facilitate gene cloning is to use transposition system independent of the P transposon. For example, the Hobo element system can be used to cause the gene mutation. However, the problem of creating a chromosomal environment that completely avoids the P transposon system has not been possible in the *Drosophila* field. This kind of approach has never been described in the field while the versatile FLP-FRT system has been publicized since 1989 (Golic and Lindquist, 1989, Cell 59,499).

Another way to overcome this is to individually recover the recombinant chromosome with an interested P insertion and the specific P[FRT]. This tedious and laborious work has been done for a collection of 496 P element-induced mutations established by the Berkeley Drosophila Genome Project (Perrimon et al., 1996, Genetics 121, 333). By using the FLP-DFS technique, 496 independent zygotic lethal mutations identified by single P-element mutations were tediously recombined with FRT chromosomes in order to analyze their germ-line clone phenotypes (Perrimon et al., 1996, Genetics 121, 333). Similarly, the same approach has been conducted in at least 7 labs in Europe. They collected only 700 recombinant chromosomes within at least 6 years. The strategy to perform similar recombination experiment is confronted with not only the prerequisite to know the location of the new P insertion for a successful recombinant but also the limitation of reaching a saturation screening since the recombination suppression exists in certain chromosome regions. These recombinants are too few to reach the 24,300 lethal chromosomes in order to reach a 87% saturation screening for the functional description of *Drosophila* essential genes (Spradling, 1999, Genetics 153, 135).

In order to overcome the foresaid drawbacks, the present invention circumvents the above difficulties by constructing an advanced version of P[FRT] insertions on the *Drosophila* second chromosome, which allows the P-directed mutagenesis to be useful for quick chromosome-wide screening and fast molecular cloning for the various FLP-FRT methods. Molecular biology technique such as inversed PCR (polymerase chain reaction) and plasmid rescue methods can be used to recover flanking genomic DNA sequences and relevant molecular properties of the genes affected by the transposon. Based on the mutated phenotypes of either germline or somatic recombinant clones produced, the biological functions can be described for the genes mutated. The integrated description of the molecular nature and biological function of *Drosophila* genes can accelerate the understanding of the functions of human gene homologues and be used as the basis for the application and development of gene-based medicines.

SUMMARY OF THE INVENTION

It is an object of the present invention to provide a method for generating a *Drosophila* clipped FRT (cFRT) chromosome insensitive to P transposase but remaining functional to yeast site-specific flippase recombinase (FLP).

It is another object of the present invention to provide a method for constructing an advanced version of the two P[FRT] insertions on the left and right arms of the *Drosophila* second chromosome, thereby forming the cFRT$^{2L2R}$ chromosome insensitive to P transposase.

It is another object of the present invention to provide a cFRT$^{2L2R}$ chromosome, which allows the P-directed mutagenesis to achieve purposes of quick chromosome-wide screening and fast molecular cloning for the various FLP-FRT methods.

It is another object of the present invention to provide a cFRT$^{2L2R}$ chromosome, which can be directly mutagenized by the P transposon and instantly followed by genetic recombination after the recovery of mutations.

According to the present invention, a method for generating a *Drosophila* clipped FRT (cFRT) chromosome insensitive to a P transposase but remaining functional to a yeast site-specific flippase recombinase (FLP), comprises steps of: (a) exposing a FRT chromosome to the P transposase for occurring a local and imprecise transposition, wherein the FRT chromosome contains a P[FRT] insertion with a selection marker gene, (b) screening the P[FRT] insertion insensitive to the P transposase to obtain screened products, (c) selecting candidate products from the screened products by further examinations, and (d) exposing the candidate products by the P transposase and selecting a desired product by the further examinations to obtain the *Drosophila* clipped FRT (cFRT) chromosome is insensitive to the P transposase but remaining functional to yeast site-specific flippase recombinase.

In accordance with the present invention, the method further comprises a step (e) of examining the actual molecular nature of the clipped insertion by PCR (polymerase chain reaction)

Preferably, the step (c) further comprises steps of: (c1) examining the screened products for both recombination capability and homozygous viability, and (c2) examining recombination accessibility of FRT sequences contained in a clipped P[FRT] insertion by the presence of the FLP to obtain the candidate products.

Preferably, the recombination capability represents the functional activity of the clipped P[FRT] insertion and its homologous location relative to that of the original P[FRT] insertion.

Preferably, the homozygous viability represents a genetic background after the chromosome's exposure to the P transposase.

Preferably, the step (d) of exposing the candidate products by the P transposase and selecting the desired product by the further examinations is repeated at least twice.

Preferably, the *Drosophila* cFRT chromosome is an isogenized homozygous viable *Drosophila* second chromosome.

Preferably, the cFRT is formed due to a target sequence, recognized by the P transposase and responsible for a P transposase transposition, which is damaged and alternated into a type of incomplete target sequence, through one of a group consisting of: (1) missing of a P5' DNA sequence region, (2) missing of a P3' DNA sequence region, and (3) missing of DNA sequences other than those defined in item (1) and in item (2).

Preferably, the *Drosophila* cFRT chromosome remains the functional activity of the cFRT insertion for a site-specific recombination in the presence of the FLP.

Preferably, an effectiveness of the *Drosophila* cFRT chromosome is monitored by a FLP-FRT system and derived modification systems thereof.

Preferably, an effectiveness of the cFRT chromosome is monitored by molecular biology methods for the description of the cFRT DNA sequences configuration.

Preferably, the *Drosophila* cFRT chromosome remains to behave normally as a wild type chromosome feasible for various genetic manipulations.

Preferably, a clipped P[FRT] insertion is alternatively moved to another chromosome from the *Drosophila* clipped FRT (cFRT) chromosome by treating the *Drosophila* cFRT chromosome with one of mutagens and X-ray.

Preferably, the *Drosophila* cFRT chromosome is alternatively used to establish a *Drosophila* cell line based on a genetic background of the *Drosophila* cFRT chromosome.

Preferably, the *Drosophila* cFRT chromosome is mutated to obtain gene mutations for further experiment.

Preferably, a molecular information of the gene mutations is recovered by retrieving flanking DNA sequences of a clipped P[FRT] insertion with a molecular biology method.

Preferably, the molecular biology method includes a plasmid rescue method, a inversed PCR method and a chromosomal walking method.

Preferably, the molecular information of the gene mutations can be recovered by a related bioinformatic manipulation.

Preferably, the related bioinformatic manipulation includes blasting databank, searching gene homologues of biological organisms, analyzing comparative genomics, and analyzing phylogenic distance and relationship.

Preferably, the functional description of the gene mutations are further analyzed based on the information obtained from the molecular biology method and the related bioinformatic manipulation by using a biological technique.

Preferably, the *Drosophila* cFRT chromosome is used to study the *Drosophila* genes located on the second chromosome and their corresponding gene homologues of other biological organisms including vertebrates, invertebrates, eukaryotes and prokaryotes.

According to another aspect, a method for generating a *Drosophila* clipped FRT$^{2L2R}$ (cFRT$^{2L2R}$) chromosome insensitive to a P transposase but remaining functional to a yeast site-specific flippase recombinase (FLP), comprises steps of: (a) exposing a double-FRT chromosome to the P transposase for occurring a local and imprecise transposition, wherein the double-FRT chromosome contains a first P[FRT] insertion with a first selection marker gene on one arm thereof and a second P[FRT] insertion with a second selection marker gene on the other arm thereof, (b) screening respectively the first P[FRT] insertion and the second P[FRT] insertion insensitive to the P transposase to obtain screened products, (c) selecting candidate products from the screened products by further examinations, and (d) exposing the candidate products by the P transposase and selecting a desired product by the further examinations to obtain the *Drosophila* clipped FRT$^{2L2R}$ (cFRT$^{2L2R}$) chromosome insensitive to the P transposase but remaining functional to yeast site-specific flippase recombinase.

In accordance with the present invention, the method further comprises a step (e) of examining the actual molecular nature of the clipped insertions by PCR.

Preferably, the step (b) further comprises steps of: (b1) screening the first P[FRT] insertion insensitive to the P transposase subject to an immobility of the first selection marker gene, and (b2) screening the second P[FRT] insertion insensitive to the P transposase from the screened products of step (b1) subject to an immobility of the second selection marker gene.

Preferably, the step (b) further comprises steps of: (b1') screening the second P[FRT] insertion insensitive to the P transposase subject to an immobility of the second selection marker gene, and (b2') screening said first P[FRT] insertion insensitive to said P transposase from screened products of step (b1') subject to an immobility of the first selection marker gene.

Preferably, the step (c) further comprises steps of: (c1) examining the screened products for both recombination capability and homozygous viability, and (c2) examining recombination accessibility of FRT sequences contained in the P[FRT] insertion by the presence of the FLP to obtain the candidate products.

Preferably, the first selection marker is different from the second selection marker.

Preferably, the *Drosophila* clipped FRT$^{2L2R}$ chromosome is alternatively generated from two *Drosophila* clipped FRT (cFRT) chromosomes (cFRT$^{2L}$ and cFRT$^{2R}$ chromosomes) by a genetic recombination method.

According to another aspect, a *Drosophila* clipped FRT (cFRT) chromosome, wherein the chromosome is insensitive to a P transposase but remains functional to a yeast site-specific flippase recombinase (FLP), comprises: a *Drosophila* second chromosome main body, and a clipped P[FRT] (cFRT) insertion immobilized by the P transposase.

In accordance with the present invention, the cFRT is formed due to a target sequence, recognized by the P transposase and responsible for a P transposase transposition, which is damaged and alternated into a type of incomplete target sequence, through one of a group consisting of: (1) missing of a P5' DNA sequence region, (2) missing of a P3' DNA sequence region, and (3) missing of DNA sequences other than those defined in item (1) and in item (2).

According to another aspect, a *Drosophila* clipped FRT$^{2L2R}$ (cFRT$^{2L2R}$) chromosome, wherein the chromosome is insensitive to a P transposase but remains functional to a yeast site-specific flippase recombinase (FLP), comprises: a *Drosophila* second chromosome main body, and a clipped P[FRT] (cFRT) insertion on a right arm (cFRT$^{2R}$) of the *Drosophila* second chromosome and a clipped P[FRT] (cFRT) insertion on a left arm (cFRT$^{2L}$) of the *Drosophila* second chromosome, wherein both the cFRT$^{2R}$ and the cFRT$^{2L}$ are immobilized by the P transposase.

In accordance with the present invention, the P[FRT] insertions on a left arm is inserted into the 3' end of the base T at 240696 bp of the AE003781 clone with the P3' end facing the centromere before being clipped, and said P[FRT] insertion a right arm is inserted into the 3' end of the base T at 11497 bp of the AE003789 clone with the P5' end pointing toward the telomere before being clipped.

Preferably, the cFRT$^{2L}$ is an imprecise excision caused by a removal of P5' region and most part of a selection marker gene thereon, wherein a fragment from bases 26 to around 2070 of FBtp0000348 locus is deleted.

Preferably, the cFRT$^{2R}$ is an imprecise excision caused by a removal of most of the P5' region and one of the FRT DNA repeats, wherein a fragment from bases 10 to 2821 of FBtp0000268 locus is deleted.

The foregoing and other features and advantages of the present invention will be more clearly understood through the following descriptions with reference to the drawings, wherein:

DETAILED DESCRIPTION OF THE PREFERRED EMBODIMENT

Figure 1:
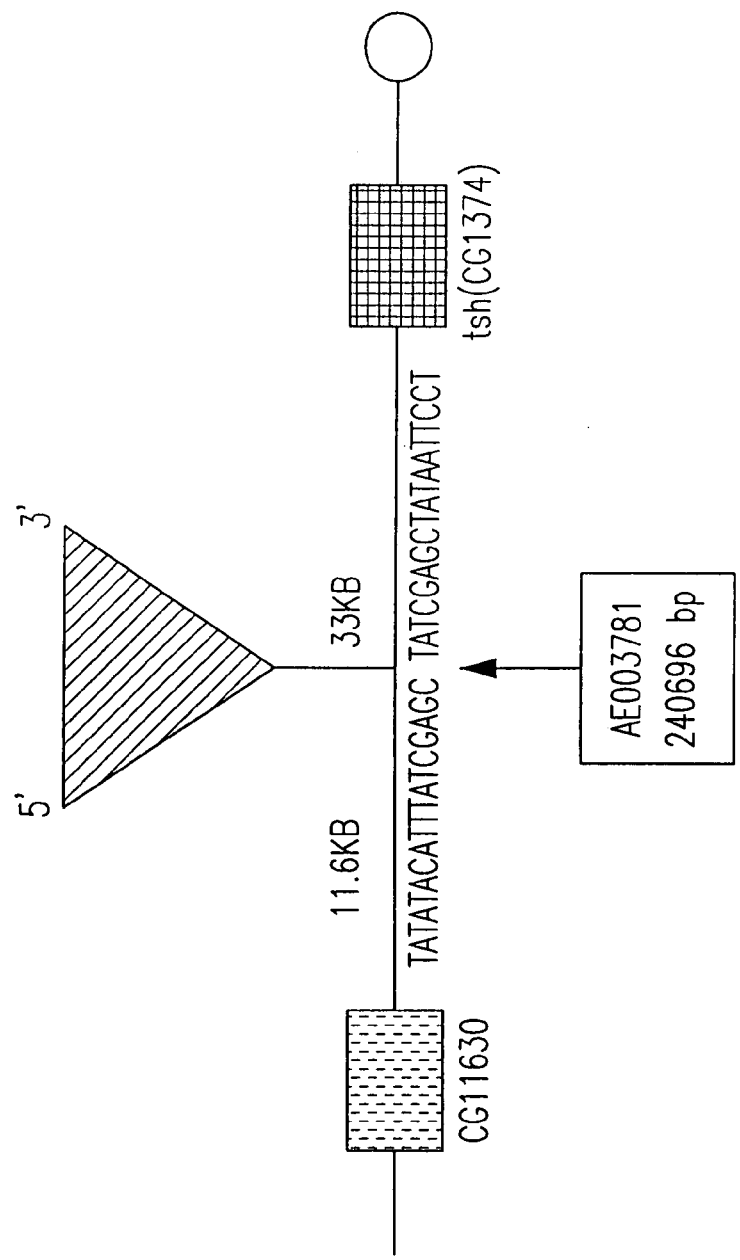
FIG. 1 (SEQ ID NO:34) is a diagram showing the position of the P[FRT] insertion on the left arm of the FRT chromosome before being clipped according to a preferred embodiment of the present invention.

The present invention will now be described more specifically with reference to the following embodiments. An advance way is provided to circumvent the previous problem by generating a new "double FRT" chromosome (where the "double FRT" chromosome was originally generated by Chou and Perrimon, 1996) which is insensitive to Δ2-3 transposase. On the double FRT chromosome, two P[FRT] insertions are located at the base of each chromosomal arm, as the targets for FLP recombinase. These double P[FRT] insertions were specifically designed to facilitate the large scale recombination clonal analysis of autosomal genes. However, the P transposase target sequences 12 contained in P[FRT] transposon are sensitive and will respond to the presence of P-transposase in the genome designed for P transposon-directed mutagenesis. To modify the double FRT chromosomes so that they are no longer sensitive to P-transposase will be the first step toward the strategy using the P-directed, but not the EMS, mutagenesis in genome-wide screening.

P donor elements are frequently excised and reinserted locally (Zhang and Spradling, 1993, Genetics 133, 361). The local transposition derivatives can be the candidates for the imprecise transposition events among which the P transposase target sequences of P[FRT] have been impaired and become insensitive to the P-transposase activity. Experimentally, several steps need to be repeatedly operated.

1. Double FRT chromosomes will be exposed to the P-transposase for local and imprecise transposition to occur.

2. Both double FRT chromosomes contain one P[FRT] insertion with mini-white$^+$ gene on one arm and another P[FRT] with rosy$^+$ gene on the other arm, wherein both the mini-white$^+$ gene and the rosy$^+$ gene are selection marker genes. The imprecise transposition event will be followed by the mosaic white eyes in one arm or the loss of rosy$^+$ gene in another arm.

3. The two P[FRT] insertions insensitive to P-transposase can be first screened subject to an immobility of miniwhite marker. The mosaic white eyes will reflect the persistent transposition of P[FRT] and the non-mosaic white-plus eyes will represent the insensitivity to the P-transposase.

4. The FRT derivatives with non-mosaic white-plus eyes will be the source for the search for the loss of rosy$^+$ gene in another arm. Derivatives fulfilled with both criteria will be examined for both the recombination capability, which represents the functional activity of P[FRT] insertion and its homologous location in compared with original P[FRT] insertion, and the homozygous viability, which represents the genetic background which is not detectably changed after its exposure to the P transposase.

5. The recombination accessibility of FRT sequences will be examined by the presence of FLP. Either germline or somatic recombination clone occurrence can be used to estimate the recombination event.

6. The stabilized or clipped P[FRT] insertion candidates will be challenged by the P-transposase for the second time.

7. The FRT sequences insensitive to P-transposase, the recombination accessibility of FRT and the homozygous viability will be examined again.

8. The steps 6 and 7 will be cycled for at least twice to ensure the transposition insensitivity and recombination accessibility and homozygous viability of the double FRT chromosomes.

9. The actual molecular nature of the clipped insertions can be examined by PCR using primer sets encompassing the target sequences of the P transposase.

After three rounds of P-transposase treatment, one derivative of the original FRT$^{2L2R}$ chromosome was selected as the modified and advanced cFRT$^{2L2R}$ chromosome which is insensitive to P-transposase challenges. However, the cFRT$^{2L2R}$ chromosome is functional for the occurring of the recombination on both 2L and 2R arm when using the original homologous P[FRT] insertions for germline clonal analysis. This homozygous viable cFRT$^{2L2R}$ chromosome is absent of both P5' inverted repeat sequences required for P transposition at both 2L and 2R P[FRT] insertions. These damages may cause this chromosome insensitive to P-transposase. In other words, the Drosophila cFRT$^{2L2R}$ chromosome contains a cFRT$^{2L2R}$ which is a clipped P[FRT] insertion on the left arm, and a cFRT$^{2R}$ which is a clipped P[FRT] insertion on the right arm. The cFRT$^{2L}$ and the cFRT$^{2R}$ are insensitive to P transposase and can not be mobilized by P transposase.

In addition, in another embodiment of the present invention, based on the imprecise transposition and local transposition, the original double FRT$^{2L2R}$ chromosome was challenged with serial rounds of Δ2-3 transposase treatment. This chromosome contains the P[FRT40A] insertion carrying rosy$^+$ eyecolor marker and the P[FRT42B] insertion carrying miniwhite$^+$ eyecolor marker. Mosaic miniwhite$^+$ eyecolor production represents the responsiveness of the P[FRT] insertion to the P transposase. After the first two rounds of challenge, derivative chromosomes with the loss of both mosaic miniwhite$^+$ and rosy$^+$ eyecolor markers are selected for further treatment as long as they are homozygously viable and functional for germline clone production based on the FLP-DFS technique. Then, further rounds of treatment will select those derivatives that produce offspring all behaved similarly to parent chromosomes in terms of being homozygous viable with compatible recombination frequency. One candidate meeting the criteria has been shown to be absent of P5' inverted repeat sequences required for P transposition in both 2L and 2R P[FRT] insertions.

This unique chromosome is deemed the "cFRT$^{2L2R}$", which particularly combines the P transposon and the FLP-FRT site-specific recombination system as an integrated one for almost 40% of Drosophila genome. It allows the direct use of P transposon as mutagen for the entry of molecular cloning drill and simultaneously the functional analysis of the genes disrupted by P insertions. This is first examined by using the FLP-DFS technique for a small scale of germline clone (GLC) screen for 36 P-induced essential loci. Specific maternal effect phenotypes can be simultaneously characterized with respect to their GLC phenotypes and their molecular properties be assigned according to the flanking genomic DNA sequences recovered by plasmid rescue and inverted PCR methods for the P insertions.

In order to describe the present invention in a greater detail, the material and method used in the embodiments are disclosed below. Flies used here were raised on standard *Drosophila* media at 25° C. unless indicated. Description of balancers and mutations can be found in Lindsley and Zimm (1992). The jumpstarter stock strain utilized here is Δ2-3(P[ry+;Δ2-3]99B) that carries a defective P element on the third chromosome at 99B which constitutively express high levels of transposase but can not itself transpose (Robertson et al. 1988). The yw; Δ2-3, Sb/TM6, Ubx stock was obtained from the Bloomington Stock Center.

The autosomal FLP-DFS technique is used for the production of germ line mosaics. To generate homozygous GLCs, females were crossed with males of genotype ywFLP$^{12}$/Y; CyO/P[ovo$^{D1}$]$^{2L}$FRT$^{2L}$ or ywFLP$^{12}$/Y; CyO/P[ovo$^{D1}$]$^{2R}$FRT$^{2R}$. These males were generated by crossing females from the ywFLP$^{12}$; CyO/Sco with the appropriate P[ovo$^{D1}$]FRT males. Females of appropriate genotypes were allowed to lay eggs for 1 day in vials and the progeny heat shocked once for 2 hrs at 37° C. in a circulating water bath over a period of 2 days when they reached late L2 to L3 larval stages as described (Chou and Perrimon, 1996). Subsequently, females of the appropriate genotype were analyzed for the presence of GLC ovaries.

Germline clones in females heterozygous for ovo$^{D1}$ were identified by ovary dissection. Females were dissected four days following eclosion. Since the ovo$^{D1}$ mutation perturbs early oogenesis, a germline clone is identified by the presence of vitellogenic egg chambers. The percentage of mosaic ovaries (% MO) is calculated by dividing the number of ovaries carrying vitellogenic egg chambers with the total number of ovaries examined.

Chromosomes derived from FRT$^{2L2R}$ were used as genomic DNA source for PCR examination. Single fly of various genotypes were used for the DNA isolation. PCR reaction was performed using touch-down melting temperature from 65-55° C. The presence of P5' and P3' regions were detected by standard PCR reaction. The primer sets used are listed below.

```
                                    (SEQ ID NO:1)
IR            (1-20)      CATGATGAAATAACATAAGG (SEQ ID NO:2)
P5' sense     (26-45)     CCGTCGAAAGCCGAAGCTTA (SEQ ID NO:3)
P5' antisense (264-232)   CCCAAGGCTCTGCTCCCACAATT (SEQ ID NO:4)
P3' sense     (2756-2775) AAACCCCACGGACATGCTAA, (SEQ ID NO:5)
P3' antisense (2878-2839) CGGCAAGAGACATCCACTTA.
```

The information of the P[lArB] element insertions is examined by inverse PCR. A sample of genomic DNA equivalent to 5-6 flies was digested with restriction enzymes Pvu II, Sau 3AI, or HinP1I separately. The digested DNA was religated with T4 DNA ligase at low DNA concentration about 0.5 ng/μl DNA. The ligation mix was extracted with phenol-chloroform, precipitated with ethanol and finally dissolved in 20 μl distilled water. 2 μl of each product was used for PCR amplification. Plac1 and Splac2 primers (designed by BDGP) were used for first P insertion 5' end PCR amplification for 25 cycles. The amplified products were diluted 50-fold, and 1 μl of the diluted product was used for a second round of PCR for 30 cycles using two nested primers, sp1 and Splac2 (designed by BDGP). Subsequently, the amplified product was sequenced directly using a nested primer, Sp1 or Splac2.

The information of the FRT$^{2L}$ and FRT$^{2R}$ insertions is examined by inverse PCR. All the reaction conditions are similar to the above description, except primers and restriction enzymes used. For FRT$^{2L}$, the Sau3A enzyme was used to digest genomic DNA, and Pry1 and Pry2 primers (designed by BDGP) were used for IPCR, and Sp3 (designed by BDGP) primer was used for DNA sequencing. For FRT$^{2R}$, the HipI enzyme was used to digest genomic DNA, and Pry1 and Pry2 primers (designed by BDGP) were used for IPCR, and Pry1 (designed by BDGP) primer was used for DNA sequencing. The primer sequences are listed below.

```
Plac1   CACCCAAGGCTCTGCTCCCACAAT     (SEQ ID NO:6)

Pry1    CCTTAGCATGTCCGTGGGGTTTGAAT   (SEQ ID NO:7)

Pry2    CTTGCCGACGGGACCACCTTATGTTATT (SEQ ID NO:8)

Splac2  GAATTCACTGGCCGTCGTTTTACAA    (SEQ ID NO:9)

Sp1     ACACAACCTTTCCTCTCAACAA       (SEQ ID NO:10)

Sp3     GAGTACGCAAAGCTTTAACTATGT     (SEQ ID NO:11)
```

As to the respect of the plasmid rescue method, a sample of genomic DNA equivalent to 5-6 flies was digested with appropriate restriction enzymes separately (e.g. XbaI and Sac II for PZ line, Hind III and Kpn I for P[lArB] line), then ligated with T4 DNA ligase to circularize the restriction fragments. The ligation mix was precipitated with ethanol and dissolved in 2 μl distilled water. 1 μl of the ligation DNA was added to 20 μl of the competent cells (DH10α). The competent cells were transformed by electroporation. The resulting colonies were pick and plasmid was extracted by using mini-preparation method. The plasmid was cut by single cut (e.g. Hind III for Plar B line) and double cut (e.g. Hind III and Sac II for Plar B line) to check size in agarose gel. Finally, the colony with correct size plasmid was incubated and sequenced using primer pry2 (designed by BDGP).

As to the respect of the method of Intrachromosomal flip-out experiment, the intrachromosomal flip-out experiment described previously (Golic and Linquist, 1989) is followed to removed miniwhite+ marker in cFRT$^{2L2R}$ chromosome. The 24-36 hours offspring from the w/Y; cFRT$^{2L2R}$/cFRT$^{2L2R}$ males crossed with ywFLP$^{12}$; CyO/Sco females were heat shock treated for 2 hrs at 37° C. The adult progeny were crossed with w/w; CyO/Sco females to examine the possible presence of white eyecolor offspring. The removal of miniwhite+ marker will produce white eyecolor progeny as the result of intrachromosomal FRT-FRT recombination.

As to the EMS mutagenesis method, 70-90 isogenized cFRT$^{2L2R}$ males were fed with a mixture of 5 mM EMS and 1% glucose solution for one day. These EMS-treated flies were mated to w/w; Sco/CyO females. White-eye male progenies which indicate that the loss-of-function of the miniwhite gene on the cFRT$^{2R}$ sequence were maintained for further analyses.

The DNA configuration of clipped FRT chromosome is determined by PCR. After IPCR and plasmid rescue manipulations, the P[FRT40A] and the P[FRT42B] insertion points were determined (the results are shown in the following embodiments). The molecular nature of the clipped P[hsneo>>, ry$^+$, FRT]$^{40A}$ and clipped P[>w$^{hs}$>, FRT]$^{42B}$ of hL18C1 were further defined by different primer sets to refine the configuration of the modified P[FRT] insertions.

The primers used are defined by the 5' to 3' sequence base pair numbered in the FBtp0000348 locus, that is the P[hsneo>>, ry+, FRT] element, and AE003781 genomic clones for clipped P[hsneo>>, ry+, FRT]$^{40A}$, and in the FBtp0000268 locus, that is the P[>w$^{hs}$>, FRT] element, and AE003789 genomic clones for clipped P[>w$^{hs}$, FRT]$^{42B}$.

4. search for (FRT$^{2L2R}$)$^c$ chromosome which is lost of ry+ eyecolor

From 427 independent FRT$^{2L2R}$ derived chromosomes which displayed nonmosaic miniwhite eyecolor, 107 ry eyecolor lines are obtained. After GLC analysis of these lines, three lines are capable of performing recombination on both 2L and 2R arms and 6 lines on 2R arm only. Others displayed destroyed or very low frequency of recombination Primers used for clipped P[hsneo>>, ry+, FRT]$^{40A}$ PCR reactions

| | | |
|---|---|---|
| 40SE | CGACGAGTTGCTTCTCCCACA | 240516-240536 in AE003781 clone |
| 40AS | GTTTCCCTCGCACTGCTATTT | 240952-240932 in AE003781 clone |
| 5' SE | CCGTCGAAAGCCGAAGCTTA | 26-45 in FBtp0000348 locus |
| 5' AS | CCCAAGGCTCTGCTCCCACAATT | 254-232 in FBtp0000348 locus |
| ry1 | CGCACGGTTTCAATCACA | 948-930 in FBtp0000348 locus |
| ry2 | GGTTACGAGGCAGCAGTTCTA | 2070-2050 in FBtp0000348 locus |
| ry3 | AACGCCCACTTCCGTATTGC | 4035-4016 in FBtp0000348 locus |
| ry4 | AATCCTGGTGCTTGCTTTCCT | 6092-6072 in FBtp0000348 locus |
| Hsp | GTAGGTCATTTGTTTGGCA | 8028-8046 in FBtp0000348 locus |
| neo | CTGATGCCGCCGTGTTC | 8587-8603 in FBtp0000348 locus |
| FRTf | CCCCGCATGGAATGGGATAAT | 9609-9629 and 10326-10346 in FBtp0000348 locus |
| FRTr | AGTCCGGTGCGTTTTT | 9948-9933 and 10665-10650 in FBtp0000348 locus |
| 3' SE | AAACCCCACGGACATGCTAA, | 14861-14880 in FBtp0000348 locus |
| 3' AS | CGGCAAGAGACATCCACTTA. | 14993-14974 in FBtp0000348 locus |

Primers used for clipped P[>w$^{hs}$>, FRT]$^{42B}$ PCR reactions are listed below

| | | |
|---|---|---|
| 42SE | TGCTCGCTTGGATGAAC | 11032-11047 in AE003789 clone |
| 42AS | AGTGGAGTGGGAGTGGA | 11600-11584 in AE003789 clone |
| 5' SE | CCGTCGAAAGCCGAAGCTTA | 26-45 in FBtp0000268 locus |
| 5' AS | CCCAAGGCTCTGCTCCCACAATT | 254-232 in FBtp0000268 locus |
| FRTf | CCCCGCATGGAATGGGATAAT | 2549-2529 and 7937-7917 in FBtp0000268 locus |
| FRTr | AGTCCGGTGCGTTTTT | 2210-2225 and 7598-7613 in FBtp0000268 locus |
| 3' SE | AAACCCCACGGACATGCTAA | 15101-15120 in FBtp0000268 locus |
| 3' AS | CGGCAAGAGACATCCACTTA | 15214-15233 in FBtp0000268 locus |

In order to describe the present invention in a greater detail, the experimental data are disclosed below. The FRT$^{2L2R}$ chromosome contains P[hsneo>>, ry+, FRT] insertion on 40A and P[>w$^{hs}$>, FRT] insertion on 42B (Chou and Perrimon, 1996). The treatment of this double P[FRT] chromosome with Δ2-3 transposase is expected to produce mosaic miniwhite+ eyecolor after the first round treatment and to recover non-miniwhite-mosaic eye color phenotype after the second challenge if the P[>w$^{hs}$>, FRT] transposon is not sensitive to Δ2-3 transposase (as shown below).

Δ2-3 transposase treatment for the recovery of the loss of mosaic miniwhite eyecolor production
1. w/Y; FRT$^{2L2R}$/FRT$^{2L2R}$ X yw/yw; Δ2-3, Sb/TM6, Ubx
2. yw/Y; FRT$^{2L2R}$/+; Δ2-3, Sb/+X yw/yw; Δ2-3, Sb/TM6, Ubx
3. yw/Y; (FRT$^{2L2R}$)$^c$/+; Δ2-3, Sb/+or TM6, Ubx X w/w; CyO/Sco
4. Pick up males without mosaic miniwhite eyecolor and set up individual lines.

After two rounds of treatments, it is also expected that the loss of ry+ eyecolor will represent the imprecise excision of P[hsneo>>, ry+, FRT] transposon (as shown below).

Selection of (FRT$^{2L2R}$)$^c$ chromosome with the loss of rosy+ eyecolor
1. w/Y; (FRT$^{2L2R}$)$^c$/(FRT$^{2L2R}$)$^c$ X+/BsY; Sp/CyO; MKRS/TM2,ry
2. +/Y; (FRT$^{2L2R}$)$^c$/CyO; MKRS/+X ry/ry
3. +/Y; (FRT$^{2L2R}$)$^c$/+; MKRS,ry/ry ability representing the mobilized P[FRT] producing a damaged FRT DNA sequences or, alternatively, a non-homologous condition with respect to P[FRT]ovo$^{D1}$ chromosome used.

The three lines, hL18, hL92, and hL97 are homozygously viable with comfortable ratio. Further treatments were focused on these three candidates.

Further treatments of chromosomes selected from previous challenges are examined by two criteria, homozygous viability and germ-line clone (GLC) recombination frequency. The lethality produced during transposase challenge would represent either the accumulation of mutations or the damage of loci flanking the previous P insertions caused by mobilization. GLC recombination will provide further information regarding the presence of FRT sequences, and possibly the degree of damage received.

The further treatments of the hL18, hL92, and hL97 lines removed hL92 as the possible candidate since 15 lines originated from hL92 all displayed homozygous lethality. This clearly showed that hL92 is very sensitive to the P transposase.

After the third round treatment, hL97 derivatives showed weak sensitivity to the P transposase since different lines displayed fluctuated homozygous viability (as shown in Table 1A).

TABLE 1A

The third round

| LINE | H.V | % |
|---|---|---|
| hL97C1 | 2/34 | 6 |
| hL97C1' | 2/24 | 8 |
| hL97C3 | 15/48 | 31 |
| hL97C3' | 10/30 | 33 |
| hL97C3" | 5/15 | 33 |
| hL97C4 | 0/21 | 0 |
| hL97C4' | 0/33 | 0 |
| hL97C5 | 13/60 | 17 |
| hL97C5' | 4/29 | 14 |
| hL97C6 | 9/41 | 22 |
| hL97C14 | 5/20 | 25 |
| hL97C16 | 0/28 | 0 |
| hL97C16' | 0/30 | 0 |

H.V: Homozygous viability is the number of homozygous flies divided by the number of total flies (homozygous + heterozygous). In theory, 33% would represent an expected homozygously viable rate.
GLC and % MO: Germ-line clonal frequency is calculated as the percentage of mosaic ovaries (% MO) of the females dissected. % MO = [number of ovaries with GLC clones/total number of ovaries examined] × 100%.

hL97C3" line was treated further since homozygously viable stock can be established. After fourth round, homozygous viability displayed smaller degree of fluctuation compared with the result from the third round (as shown in Table 1B)

TABLE 1B

The fourth round

| LINE | H.V. | % | 2LGLC | % MO | 2RGLC | % MO |
|---|---|---|---|---|---|---|
| hL97C3"C1 | 36/161 | 22 | 33/40 | 83 | | |
| hL97C3"C3 | 53/182 | 29 | | | | |
| hL97C3"C4 | 46/158 | 29 | | | | |
| hL97C3"C7 | 139/446 | 31 | 129/194 | 67 | 87/100 | 8 |
| hL97C3"C8 | 29/105 | 28 | | | | |
| hL97C3"C10 | 106/316 | 34 | | | | |
| hL97C3"C12 | 103/445 | 23 | 26/30 | 87 | 14/14 | 100 |
| hL97C3"C14 | 12/90 | 8 | 54/84 | 64 | 41/48 | 85 |
| hL97C3"C15 | 130/420 | 31 | 25/46 | 54 | 26/36 | 72 |
| hL97C3"C16 | 6/45 | 13 | | | | |
| hL97C3"C18 | 18/111 | 16 | | | | |
| hL97C3"C20 | 70/351 | 20 | 40/64 | 63 | 71/98 | 72 |
| hL97C3"C21 | 47/326 | 14 | | | | |

However, only 8 out of 13 lines can be established as homozygously viable stocks. The result obtained from fifth round of treatment (as shown in Table 1C) suggests that few hL97C3" derivatives can tolerate the transposase challenges.

TABLE 1C

The fifth round

| LINE | HV | % | 2L GLC | % MO | 2RGLC | % MO |
|---|---|---|---|---|---|---|
| hL97C3"C1C1 | 39/174 | 22 | 50/78 | 64 | 17/26 | 65 |
| hL97C3"C3C1 | 19/93 | 20 | 38/66 | 58 | 22/30 | 73 |
| hL97C3"C3C2 | 25/107 | 23 | 19/28 | 68 | 16/20 | 80 |
| hL97C3"C7C2 | 18/48 | 38 | | | | |
| hL97C3"C7C3 | 36/164 | 28 | 26/38 | 68 | 46/58 | 79 |
| hL97C3"C7C5 | 13/48 | 27 | | | | |
| hL97C3"C15C1 | 40/81 | 49 | | | | |

After the third round of transposase treatment, 2 independent derivatives, hL18c1 and hL18c3 were picked up for further treatment since both are homozygously viable and have 55 to 77% recombination frequency on both 2L and 2R arms (data not shown). After the fourth round, 11 derivatives from hL18c1 all display expected homozygous viability ratio and constant recombination frequency ranging from 55 to 80 (as shown in Table 2A).

TABLE 2A hL18C1

| LINE | HV | % | 2L GLC | % MO | 2R GLC | % MO |
|---|---|---|---|---|---|---|
| hL18c1c1 | 95/280 | 32 | 43/64 | 67 | 41/58 | 71 |
| hL18c1c2 | 88/248 | 35 | 35/56 | 63 | 38/56 | 68 |
| hL18c1c3 | 90/229 | 39 | 45/68 | 66 | 26/34 | 76 |
| hL18c1c4 | 107/231 | 46 | 83/98 | 85 | 40/52 | 77 |
| hL18c1c5 | 89/231 | 38 | 66/82 | 80 | 28/50 | 56 |
| hL18c1c6 | 97/232 | 42 | 76/110 | 69 | 30/54 | 56 |
| hL18c1c7 | 79/226 | 35 | 108/182 | 59 | 50/66 | 76 |
| hL18c1c8 | 82/232 | 35 | 57/90 | 63 | 25/42 | 60 |
| hL18c1c9 | 116/282 | 41 | 74/118 | 63 | 5/12 | 42 |
| hL18c1c10 | 89/251 | 35 | 60/90 | 67 | 30/40 | 75 |
| hL18c1c11 | 104/302 | 34 | 43/68 | 63 | 29/52 | 56 |

These results meet the criteria as the hL18c1 chromosome is devoid of transposase sensitivity. Nevertheless, it is still able to perform the FLP-FRT recombination with a comfortable frequency.

1 out of 11 hL18C3 derived lines showed homozygous lethality. In comparison with hL18c1, this suggests that the hL18c3 chromosome is remaining sensitive to the P transposase in a low frequency manner (as shown in Table 2B).

TABLE 2B hL18C3

| LINE | HV | % | 2LGLC | % MO | 2RGLC | % MO |
|---|---|---|---|---|---|---|
| hL18c3c1 | 76/265 | 29 | 71/94 | 76 | 51/74 | 69 |
| hL18c3c2 | 120/301 | 40 | 51/82 | 62 | 26/58 | 45 |
| hL18c3c3 | 83/218 | 38 | 77/110 | 70 | 32/56 | 57 |
| hL18c3c4 | 101/255 | 40 | 139/196 | 71 | 49/56 | 88 |
| hL18c3c5 | 0/120 | 0 | | | | |
| hL18c3c6 | 144/293 | 49 | 27/58 | 47 | 37/62 | 60 |
| hL18c3c7 | 97/262 | 32 | 41/74 | 55 | 22/50 | 44 |
| hL18c3c8 | 75/231 | 32 | 29/48 | 60 | 22/40 | 55 |
| hL18c3c9 | 95/298 | 32 | 30/58 | 52 | 30/60 | 60 |
| hL18c3c10 | 85/245 | 35 | 60/82 | 73 | 8/16 | 50 |
| hL18c3c11 | 101/240 | 42 | 23/56 | 41 | 41/64 | 64 |

The molecular nature of hL18C1 was further defined first by IPCR to define the loci of P[hsneo>>, ry+, FRT]$^{40A}$ and P[>w$^{hs}$>, FRT]$^{42B}$, and second by different primer sets to refine the configuration of the modified P[FRT] insertions.

Figure 2:
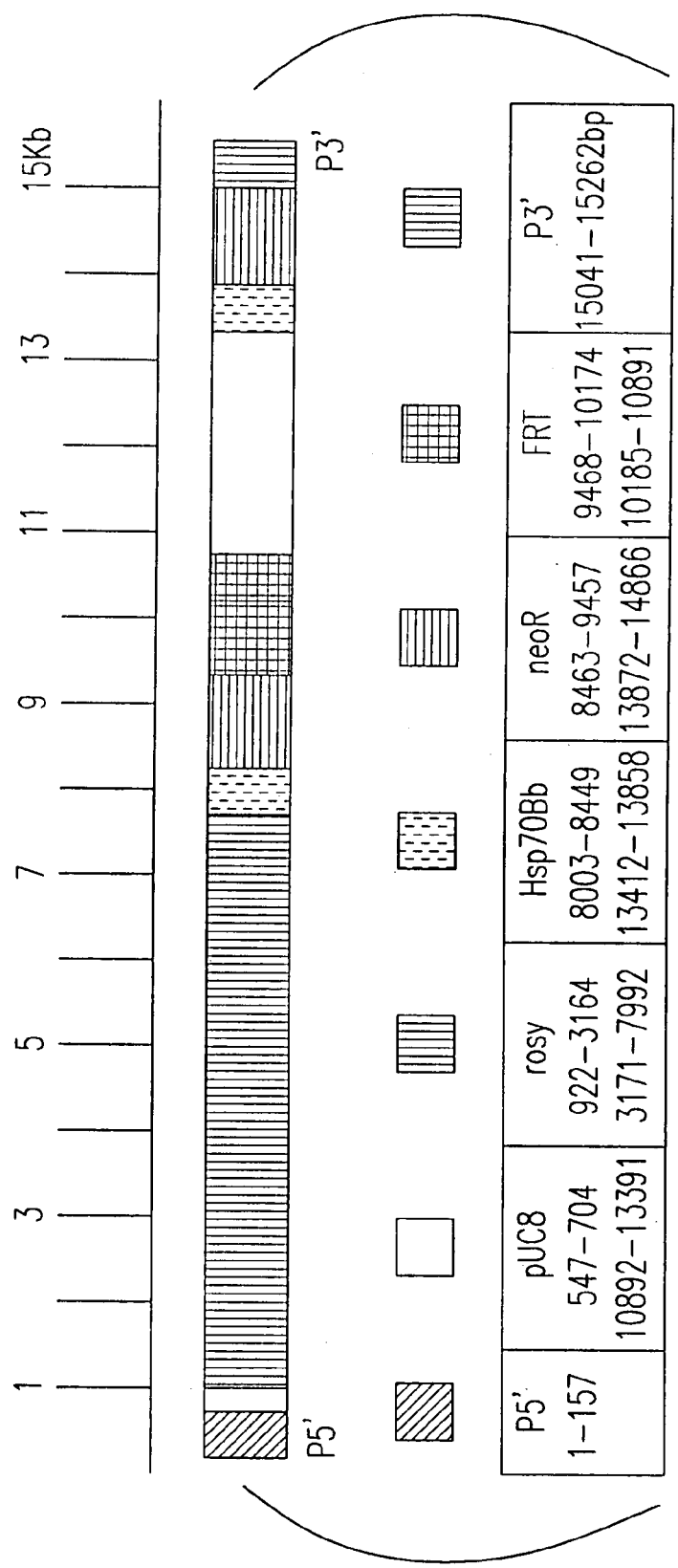
FIG. 2 is a diagram showing the P[FRT] insertion on the left arm of the FRT chromosome before being clipped according to a preferred embodiment of the present invention.
Figure 3:
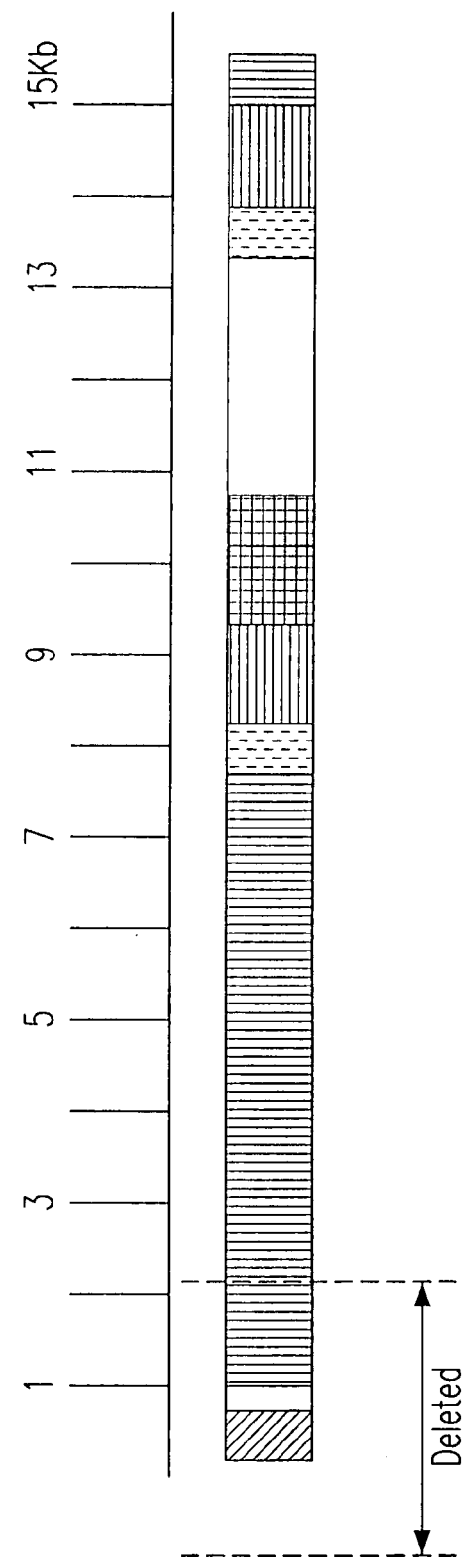
FIG. 3 is a diagram showing the P[FRT] insertion on the left arm of the FRT chromosome after being clipped according to a preferred embodiment of the present invention.

Please refer to FIG. 1, which is a diagram showing the position of the P[FRT] insertion on the left arm of the FRT chromosome before being clipped according to a preferred embodiment of the present invention. Originally, P[hsneo>>, ry+, FRT]40A is inserted into the 3' end to the base T at 240696 bp of the AE003781 clone with the P3' end facing centromere. Please refer to FIG. 2, which is a diagram showing the P[FRT] insertion on the left arm of the FRT chromosome before being clipped according to a preferred embodiment of the present invention. The P[FRT] insertion on the left arm includes P5' region (1-157 bp), pUC8 (547-704 bp and 10892-13391 bp), rosy (922-3164 bp and 3171-7992 bp), Hsp70Bb (8003-8449 bp and 13412-13858 bp), neoR (8463-9457 bp and 13872-14866 bp), FRT (9468-10174 bp and 10185-10891 bp), and P3' region (15041-15262 bp). Please refer to FIG. 3, which is a diagram showing the P[FRT] insertion on the left arm of the FRT chromosome after being clipped according to a preferred embodiment of the present invention. In clipped P[hsneo>>, ry+, FRT]40A, imprecise excision caused the removal of P5' region and most part of the rosy+ DNA segment, e.g. fragment from bases 26 to around 2070 of FBtp0000348 locus were known being deleted.

Figure 4:
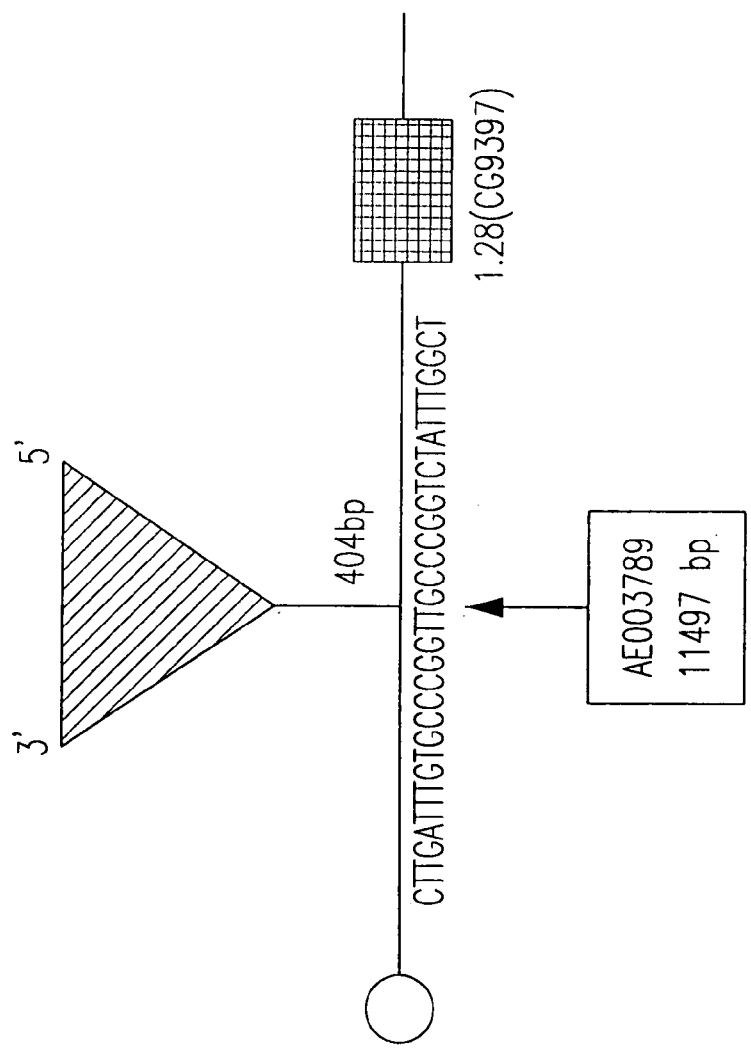
FIG. 4 (SEQ ID NO:35) is a diagram showing the position of P[FRT] insertion on the right arm of the FRT chromosome before being clipped according to a preferred embodiment of the present invention.
Figure 5:
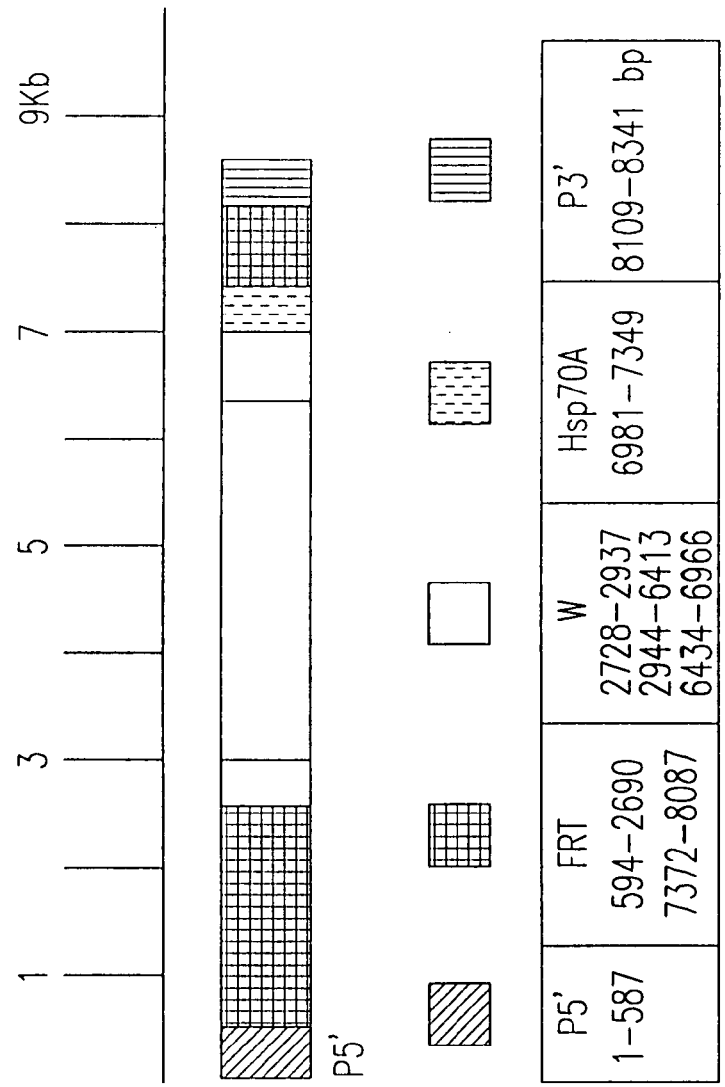
FIG. 5 is a diagram showing the P[FRT] insertion on the right arm of the FRT chromosome before being clipped according to a preferred embodiment of the present invention.
Figure 6:
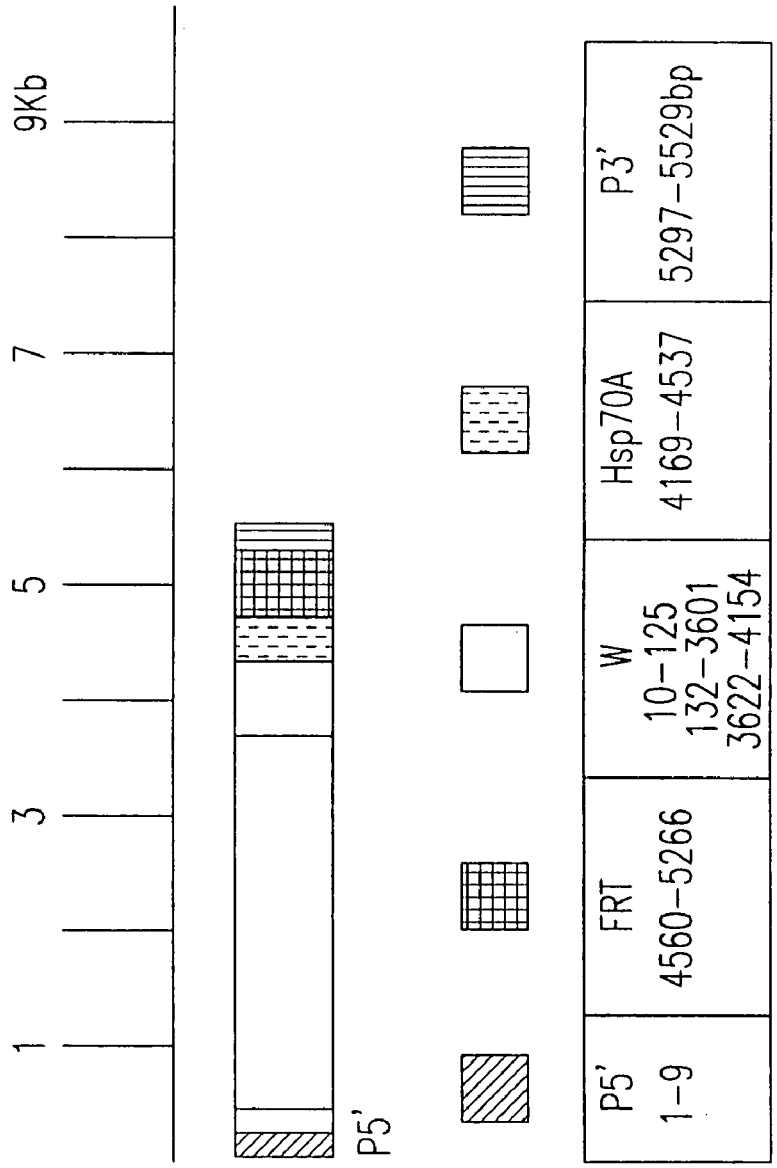
FIG. 6 is a diagram showing the P[FRT] insertion on the right arm of the FRT chromosome after being clipped according to a preferred embodiment of the present invention.

Please refer to FIG. 4, which is a diagram showing the position of the P[FRT] insertion on the right arm of the FRT chromosome before being clipped according to a preferred embodiment of the present invention. P[>whs>, FRT]42B is originally inserted into the 3' end to the base T at 11497 bp of the AE003789 clone with the P5' end pointing toward telomere. Please refer to FIG. 5, which is a diagram showing the P[FRT] insertion on the right arm of the FRT chromosome before being clipped according to a preferred embodiment of the present invention. The P[FRT] insertion on the right arm includes P5' region (1-587 bp), FRT (594-2690 bp and 7372-8078 bp), mini-white (2728-2937 bp, 2944-6413 bp and 6434-6966 bp), Hsp70A (6981-7349 bp), and P3' region (15041-15262 bp). Please refer to FIG. 6, which is a diagram showing the P[FRT] insertion on the right arm of the FRT chromosome after being clipped according to a preferred embodiment of the present invention. Most of the most P5' region and one of the FRT DNA repeats, e.g. bases 10 to 2821 of FBtp0000268 locus, were deleted in the clipped P[>whs>, FRT]42B during this trimming action. The clipped P[FRT] insertion on the right arm includes P5' region (1-9 bp), FRT (4560-5266 bp), mini-white (10-125 bp, 132-3601 bp and 3622-4154 bp), Hsp70A (4169-4537 bp), and P3' region (5297-5529 bp).

The P transposase recognizes the 5' and 3' ends including inverted repeat and other internal sequences as targets of transposase for P transposition (Kaufman et al., 1989). The configuration suggests that both clipped P[hsneo>>, ry+, FRT]$^{40A}$ and clipped P[>w$^{hs}$>, FRT]$^{42B}$ in this new chromosome are lacking of the P5' region. Nevertheless, FRT DNA sequences remain and are still fully functional for FRT-based site-specific recombination. Due to the clipping away of the two P5' substrate regions, hL18c1 are renamed the "clipped FRT$^{2L2R}$ (cFRT$^{2L2R}$)" chromosome for the clipped P[FRT]$^{2L}$•clipped P[FRT]$^{2R}$ transposon insertions on the second chromosome.

P[>w$^{hs}$>, FRT] insertion on 42B provides the miniwhite marker of FRT$^{2L2R}$ chromosome. The miniwhite marker can be removed by intrachromosomal recombination between the two FRT DNA sequences (Golic and Lindquist, 1989). To perform P-directed mutagenesis scheme using P[lacW] instead of P[ry+] transposon, the miniwhite marker from cFRT$^{2L2R}$ chromosome was attempted to be removed. In contrast to positive result when hL18 is treated, the miniwhite marker cannot be removed from cFRT chromosome. At least five trials were done by different people showing the same result. Though the clipped P[>w$^{hs}$>, FRT] insertion on 42B can accept the P[>w$^{hs}$>, FRT] insertion on the homologous chromosome for interchromosomal recombination, it can not perform the intrachromosomal recombination.

To search for cFRT$^{2L2R}$ chromosome with white-minus eyecolor, about 18,000 flies were examined after EMS treatment of the isogenized IcFRT$^{2L2R}$ #60 (as shown in Table 3). 4 flies, EMS1 to 4, were selected.

TABLE 3

Germline clonal analysis of isogenized cFRT$^{2L,2R}$ chromosome

| | MO % | | Hatching rate in GLC | | DE % | |
|---|---|---|---|---|---|---|
| IcFRT$^{#60}$-2L | 156/184 | 0.85% | 493/595 | 0.83% | 5/595 | 0.0084% |
| IcFRT$^{#60}$-2R | 153/178 | 0.86% | 436/450 | 0.97% | 3/450 | 0.0067% |
| IcFRT$^{#61}$-2L | 148/162 | 0.91% | 563/600 | 0.94% | 6/600 | 0.0100% |
| IcFRT$^{#61}$-2R | 132/158 | 0.84% | 417/430 | 0.97% | 3/430 | 0.0070% |

MO %: mosaic ovary (NO. of developed ovary versus total ovary).
Hatch rate in GLC: NO. of hatched eggs/total eggs laid.
DE %: NO. of dead embryos/total eggs in germline clone analysis EMS1 had cream-colored eyes and the others with white and red mosaic eyecolors. After these 4 males were crossed with w/w; Sco/CyO females, different results for these 4 chromosomes were found. All the progeny of EMS1 had red eyes. EMS3 turned out to be male sterile. The progeny of EMS2 and EMS4 had either red eyes or white eyes with the ratio of 1:1. One red-eyed male and 5 white-eyed males from the EMS2 progeny and one white-eyed male from the EMS4 progeny were collected for further analyses. These putative cFRT$^{2R2LW}$ chromosomes were denominated NR2-1, NW2-1 to NW2-5 and NW4, respectively.

To examine the recombination capacities of these modified chromosomes, germline clone analysis is generated. It turned out that the hatching rate of each strain was similar to the original untreated strain IcFRT$^{2L2R}$#60 (as shown in Table 4), and no particular embryonic phenotype was found.

TABLE 4

Hatching rate in GLC of cFRT$^{2L2RW}$ chromosomes

| | GLC tested | Hatching rate in GLC |
|---|---|---|
| IcFRT$^{60}$ | 2L | 493/595 = 82.9% |
| | 2R | 436/450 = 96.9% |
| NR2-1 | 2L | 243/268 = 90.7% |
| | 2R | 208/227 = 91.6% |
| NW2-1 | 2L | 178/200 = 89.0% |
| | 2R | 160/192 = 83.3% |
| NW2-2 | 2L | 168/189 = 88.9% |
| | 2R | 160/175 = 91.4% |
| NW2-3 | 2L | 120/141 = 85.1% |
| | 2R | 215/227 = 94.7% |
| NW2-4 | 2L | 159/179 = 88.8% |
| | 2R | 159/187 = 85.0% |
| NW2-5 | 2L | 131/155 = 84.5% |
| NW4 | 2L | 211/219 = 96.3% |
| | 2R | 173/185 = 93.5% |

After isogenization, it was confirmed that the chromosome behaved as a wild type chromosome (as shown in Table 3). This cFRT$^{2L2R}$ chromosome was used for a pioneer screen for the searching of essential loci on the second chromosome with specific maternal effects.

The failure to remove the miniwhite marker enforced us to use P[ry+] transposon as the mutagen. Two schemes described below were designed.

A.
1. +/Y; SM1/Sco; ry/ry X P[lArB]/P[lArB]
2. P[lArB]/Y; SM1/+; ry/+X w/w; cFRT/cFRT
3. yw/Y; Sco/CyO, Δ2-3; MKRS/+X P[lArB]/w; cFRT/SM1; +/+
4. P[lArB]/Y; cFRT/CyO, Δ2-3; MKRS/+X SM1/Sco;ry/ry
5. look for (+/Y; cFRT/SM1 or Sco; MKRS/ry) males with ry+eyecolor 6. (+/Y; cFRT/SM1 or Sco; MKRS/ry) X SM1/Sco; ry/ry
   a. if all Sb flies are with ry⁺ eyecolor, the P transposon may be on the MKRS chromosome
   b. if some Sb and some Sb+ flies are with ry⁺ eyecolor, the P transposon may be on the cFRT or the fourth chromosome.
   c. if all Sb and all Sb+ flies are with ry⁺ eyecolor, there may be multiple insertions on autosomes.
7. Select P transposon on cFRT chromosome and determine their homozygous lethality.

B.
1. P[lArB]/P[lArB]; cFRT/cFRT; ry/ry X yw/Y; Sco/CyO, Δ2-3; MKRS/+
2. P[lArB]/Y; cFRT$^{2L2R}$/CyO, Δ2-3; MKRS/+X+/+; Sco/CyO; ry/ry
3. Look for (+/Y; cFRT$^{2L2R}$/CyO or Sco; MKRS/ry) males with ry+ eyecolor
4. (+/Y; cFRT/SM1 or Sco; MKRS/ry) with ry+ eyecolor X+/+; Sco/CyO; ry/ry
5. examine the location of P[lArB] insertions as that described in A. scheme.

Several different P[lArB] insertions on X chromosome were tested for their transposition efficiency. P[lArB] insertions with normal efficiency (Spradling et al., 1999) of transposition will be candidates for future large scale screening. The P transposon on X chromosome was used as the mutagen, determined whether the P-induced mutations on the second chromosome were created by the disruption of essential genes causing the homozygous lethality, analyzed the possible maternal functions based on the FLP-DFS technique (Chou and Perrimon, 1996), and recovered genomic DNA segments flanking P insertions by plasmid rescue and inversed PCR methods.

From 189 lines with P insertions on the cFRT$^{2L2R}$ chromosome, 36 homozygous lethal lines are obtained. The 19% homozygous lethal rate is compatible with previous P-induced homozygous rate (Spradling et al., 1999). This further demonstrated that the cFRT$^{2L2R}$ can perform normal as a wild type chromosome for P transposition. As shown in Table 5, the four classes of zygotic lethals with specific maternal effect phenotypes (Perrimon et al., 1989): germ cell lethal (GCL) phenotype, abnormal oogenesis (AO) phenotype, maternal effect (ME) and maternal effect rescuable (MER) and no maternal effect (NME) phenotype can be assigned to the essential loci on the cFRT$^{2L2R}$ chromosome.

TABLE 5

Result of the primary screen for essential loci with specific maternal effects using the cFRT2L2R chromosome

| Stock # | 2L | 2R | Phenotype | Gene | Function | Allele |
|---|---|---|---|---|---|---|
| Germ Cell Lethal phenotype | | | | | | |
| 1168c2 | no eggs | NME | arrested at stage2 | CG13790 | | New |
| | | | | CG13791 | | New |
| a150a | no eggs | NME | arrested at stage2 | AC3 | Guanylate cyclases | New |
| | | | | CG1512 | cell cycle regulator (cullin) | New |
| a138 | no eggs | | arrested at stage2 | CycE | cell cycle regulator (cyclin) | Known |
| | | | | | | Known |
| R069 | no eggs | NME | arrested at stage2 | CG9586/Cg | | New |
| 1168-2 | no eggs | NME | arrested at stage2 | | | ND |
| a137 | NME | no eggs | arrested at stage2 | | | ND |
| 1168e | NME | no eggs | arrested at stage2 | | | ND |
| Abnormal Oogenesis phenotype | | | | | | |
| 1164f2 | AO | NME | arrested at stage6 | BcDNA:GM 14618 | translation factor | New |
| b26b | NME | AO | arrested at stage6 | CG14040 | transporter | New |
| | | | | Sin3A | transcription factor | Known |
| b235 | NME | AO | arrested at stage6 | | | ND |
| F263 | NME | AO | arrested at stage6 | beta-tub56D | | New |
| F284 | NME | AO | arrested at stage7 | CG11508 | snRNA | New |
| 594-28 | NME | AO | arrested at stage7 | CG12864 | motor protein | New |
| Embryo with specific Maternal Effect phenotype | | | | | | |
| Y016-1 | NME | MER | posterior group | CG17280/2R | Cytochrome C subunit | New |
| b54a | NME | MER | posterior group | Or45b-CG12931 | Olfactory receptor | New |
| | | | | CG1888 | NLS BP | New |
| b347 | MER | NME | denticle belts fusion | CG10685 | enzyme (RNA PolI) | New |
| b241b | ME | NME | dorsalized | dorsal | transcription factor | Known |
| a210a | MER | NME | denticle belts fusion | Out at first | | Known |
| | | | like gap gene | bratCGJ0719 | transcription factor transmembrane | Known |
| 4799 | NME | MER | lawn-of-denticles | tout-velu | protein | Known |
| b345 | ME | NME | denticle belts fusion | | | ND |
| a350 | NME | MER | (like kismet) no phenotype | | | ND |

TABLE 5-continued

Result of the primary screen for essential loci with specific maternal effects using the cFRT2L2R chromosome

| Stock # | 2L | 2R | Phenotype | Gene | Function | Allele |
|---|---|---|---|---|---|---|
| No maternal effect phenotype | | | | | | |
| a22 | NME | | | CG12052 | transcription factor | New |
| b181 | NME | NME | denticle fusion | kismet | | Known |
| 1168f1 | NME | NME | | | | ND |
| 1164b | NME | NME | | | | ND |
| 594c1 | NME | NME | | | | ND |
| 1164 | NME | NME | | | | ND |
| 1164c4 | NME | NME | | | | ND |
| 1164a13 | NME | NME | | | | ND |
| a194 | NME | NME | | | | ND |
| a256 | NME | NME | | | | ND |
| a172b | NME | NME | | | | ND |
| a301 | NME | NME | | | | ND |
| b187 | NME | NME | | | | ND |
| b140b | NME | NME | | | | ND |
| b30a | NME | NME | | | | ND |

Germ cell lethal phenotype is assigned if no eggs is laid for more than 15 GLC females examined.
AO: abnormal oogenesis;
MER: paternal rescuable maternal effect;
ME: strict maternal effect
NME: no maternal effect;
ND: molecular properties not yet determined.
When there is no known alleles in FlyBase databank, the P insertion is said to be assigned as a new allele.

Either left or right arms can be the target of the P transposition and be analyzed for their germline clone phenotype. This is the first time to demonstrate that a double FRT chromosome can be used for GLC analysis for both arms simultaneously after P mutagenesis.

The molecular nature of these essential loci were immediately determined. From mutation lines analyzed, both new and known alleles were recovered. Known genes with specific GLC embryonic phenotypes were recovered. By complementation test and DNA sequences comparison, known genes with compatible phenotypical descriptions, for example, dorsal (b241b), tout-velu (4799) and kismet (b181), were confirmed both molecularly and genetically. These cases demonstrated that the mutation phenotypes obtained were resulted from the disruption of essential loci by P insertions instead of the presentation of unknown endogenous chromosomal denaturation created during the process of establishing the cFRT$^{2L2R}$ chromosome.

This preliminary result clearly demonstrates that the cFRT$^{2L2R}$ chromosome will be feasible for the a large scale screen using the P-transposon as the mutagen to disrupt 95% essential loci on the *Drosophila* second chromosome.

While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. A *Drosophila* clipped $FRT^{2L2R}$ ($cFRT^{2L2R}$) chromosome, wherein said chromosome is incapable of reacting with a P transposase but capable of reacting with a yeast site-specific flippase recombinase (FLP), comprising:
   a *Drosophila* second chromosome main body; and
   a clipped P[FRT] (cFRT) insertion on a right arm ($cFRT^{2R}$) of said *Drosophila* second chromosome and a clipped P[FRT] (cFRT) insertion on a left arm ($cFRT^{2L}$) of said *Drosophila* second chromosome, wherein both said $cFRT^{2R}$ and said $cFRT^{2L}$ are immobilized by said P transposase.

2. The *Drosophila* $cFRT^{2L2R}$ chromosome according to claim 1, wherein said P[FRT] insertions on a left arm is inserted into the 3' end of the base T at 240696 bp of the AE003781 clone with the P3' end facing the centromere before being clipped, and said P[FRT] insertion on a right arm is inserted into the 3' end of the base T at 11497 bp of the AE003789 clone with the P5' end pointing toward the telomere before being clipped.

3. The *Drosophila* $cFRT^{2L2R}$ chromosome according to claim 1, wherein said $cFRT^{2L}$ is an imprecise excision caused by a removal of P5' region and of a selection marker gene thereon, wherein a fragment from bases 26 to around 2070 of FBtp0000348 locus is deleted.

4. The *Drosophila* $cFRT^{2L2R}$ chromosome according to claim 1, wherein said $cFRT^{2R}$ is an imprecise excision caused by a removal of most of the P5' region and one of the FRT DNA repeats, wherein a fragment from bases 10 to 2821 of FBtp0000268 locus is deleted.

* * * * *